United States Patent [19]
Lax et al.

[11] Patent Number: 5,630,794
[45] Date of Patent: May 20, 1997

[54] CATHETER TIP AND METHOD OF MANUFACTURING

[75] Inventors: Ronald G. Lax, Grassvalley; James A. Baker, Palo Alto, both of Calif.

[73] Assignee: Vidamed, Inc., Menlo Park, Calif.

[21] Appl. No.: 311,090

[22] Filed: Sep. 23, 1994

Related U.S. Application Data

[63] Continuation-in-part of Ser. No. 929,638, Aug. 12, 1992, abandoned, and a continuation-in-part of Ser. No. 12,370, Feb. 2, 1993, Pat. No. 5,370,675, and a continuation-in-part of Ser. No. 62,364, May 13, 1993, Pat. No. 5,435,805.

[51] Int. Cl.$^6$ ................................................. A61B 17/39
[52] U.S. Cl. ......................................................... 604/22
[58] Field of Search ................................ 604/19–22, 53, 604/164, 280; 606/39, 45; 607/96, 98–102, 113–116, 138, 156; 601/2

[56] References Cited

U.S. PATENT DOCUMENTS

| | | |
|---|---|---|
| 32,066 | 1/1886 | Leveen . |
| 1,879,249 | 9/1932 | Hansaker ........................... 604/280 |
| 1,950,788 | 3/1934 | Ewerhardt et al. . |
| 1,968,997 | 8/1934 | Drucker . |
| 2,008,526 | 7/1935 | Wappler et al. . |
| 2,022,065 | 11/1935 | Wappler . |
| 2,047,535 | 7/1936 | Wappler . |
| 2,118,631 | 5/1938 | Wappler . |
| 2,710,000 | 6/1955 | Cromer et al. . |
| 3,230,957 | 1/1966 | Seifert . |
| 3,339,542 | 9/1967 | Howell . |
| 3,556,079 | 1/1971 | Omizo et al. . |
| 3,595,239 | 7/1971 | Petersen . |
| 3,598,108 | 8/1971 | Jamshidi et al. . |
| 3,682,162 | 8/1972 | Colyer . |
| 3,828,780 | 8/1974 | Morrison, Jr. . |
| 3,835,842 | 9/1974 | Iglesias . |
| 3,840,016 | 10/1974 | Lindemann . |
| 3,850,175 | 11/1974 | Iglesias . |

(List continued on next page.)

FOREIGN PATENT DOCUMENTS

| | | |
|---|---|---|
| 10858/92 | 8/1992 | Australia . |
| 0219216A1 | 4/1987 | European Pat. Off. . |
| 0370890 | 5/1990 | European Pat. Off. . |
| 0453071 | 10/1991 | European Pat. Off. . |
| 0495443 | 7/1992 | European Pat. Off. . |
| 521264A2 | 1/1993 | European Pat. Off. . |
| 2848484 | 5/1979 | Germany . |
| 2941060A1 | 4/1980 | Germany . |
| 3218314 | 6/1983 | Germany . |
| 3247793A1 | 7/1983 | Germany . |
| 3844131 | 12/1988 | Germany . |
| 3838840 | 5/1990 | Germany . |
| 2121675 | 5/1990 | Japan . |
| 9007303 | 7/1990 | WIPO . |
| WO911213 | 8/1991 | WIPO . |
| 9116859 | 11/1991 | WIPO . |
| 9207622 | 5/1992 | WIPO . |
| WO92/10142 | 6/1992 | WIPO . |
| 9221285 | 12/1992 | WIPO . |
| 9221278 | 12/1992 | WIPO . |

(List continued on next page.)

OTHER PUBLICATIONS

Standard Urology Product Catalog, CIRCON ACMI: Stanford (1992).
Chang, Raymond J. et al, American Heart Journal, 125: 1276–1283 (May, 1993).
Cosman, Eric R. et al, Sterostatic and Functional Neurosurgery, pp. 2490–2499 (Date Unknown).
Diasonics, Brochure DIA 2000 171 CRF May 1988.

(List continued on next page.)

*Primary Examiner*—Manuel Mendez
*Attorney, Agent, or Firm*—Flehr, Hohbach, Test, Albritton & Herbert

[57] ABSTRACT

A medical device having a unique tip has been described. Furthermore, a process of manufacturing the unique tip is described. The medical device of this invention penetrates tissues within a body cavity and precisely reaches the selected target to deliver energy or substance to the tissue.

26 Claims, 8 Drawing Sheets

U.S. PATENT DOCUMENTS

| | | | |
|---|---|---|---|
| 3,858,577 | 1/1975 | Bass et al. . | |
| 3,884,237 | 5/1975 | O'Malley et al. . | |
| 3,924,628 | 12/1975 | Droegemueller et al. . | |
| 3,939,840 | 2/1976 | Storz . | |
| 3,941,121 | 3/1976 | Olinger et al. . | |
| 3,942,530 | 3/1976 | Northeved . | |
| 3,948,270 | 4/1976 | Hasson . | |
| 3,991,770 | 11/1976 | Leveen . | |
| 4,011,872 | 3/1977 | Komiya . | |
| 4,119,102 | 10/1978 | Leveen . | |
| 4,121,592 | 10/1978 | Whalley . | |
| 4,136,566 | 1/1979 | Christensen . | |
| 4,137,920 | 2/1979 | Bonnet . | |
| 4,154,246 | 5/1979 | Leveen . | |
| 4,204,549 | 5/1980 | Paglione . | |
| 4,224,929 | 9/1980 | Furihata . | |
| 4,228,809 | 10/1980 | Paglione | 128/804 |
| 4,237,898 | 12/1980 | Whalley . | |
| 4,267,828 | 5/1981 | Matsuo . | |
| 4,295,467 | 10/1981 | Mann et al. . | |
| 4,307,720 | 12/1981 | Weber, Jr. . | |
| 4,311,145 | 1/1982 | Esty et al. . | |
| 4,311,154 | 1/1982 | Sterzer et al. . | |
| 4,312,364 | 1/1982 | Convert et al. . | |
| 4,336,809 | 6/1982 | Clark . | |
| 4,375,220 | 3/1983 | Matvias . | |
| 4,397,314 | 8/1983 | Vaguine . | |
| 4,402,311 | 9/1983 | Hattori . | |
| 4,405,314 | 9/1983 | Cope . | |
| 4,411,266 | 10/1983 | Cosman . | |
| 4,448,198 | 5/1984 | Turner . | |
| 4,452,236 | 6/1984 | Utsugi . | |
| 4,470,407 | 9/1984 | Hussein | 606/2 |
| 4,494,539 | 1/1985 | Zenitani et al. . | |
| 4,552,554 | 11/1985 | Gould et al. . | |
| 4,562,838 | 1/1986 | Walker . | |
| 4,565,200 | 1/1986 | Cosman . | |
| 4,568,329 | 2/1986 | Mahurkar . | |
| 4,580,551 | 4/1986 | Siegmund et al. . | |
| 4,594,074 | 6/1986 | Anderson et al. . | |
| 4,601,296 | 7/1986 | Yerushalmi . | |
| 4,612,940 | 9/1986 | Kasevich et al. . | |
| 4,658,836 | 4/1987 | Turner . | |
| 4,660,560 | 4/1987 | Klein . | |
| 4,669,475 | 6/1987 | Turner . | |
| 4,672,962 | 6/1987 | Hershenson . | |
| 4,676,258 | 6/1987 | Inokuchi et al. . | |
| 4,681,122 | 7/1987 | Winters et al. . | |
| 4,682,596 | 7/1987 | Bales et al. . | |
| 4,697,595 | 10/1987 | Breyer et al. . | |
| 4,700,716 | 10/1987 | Kasevich et al. . | |
| 4,706,681 | 11/1987 | Breyer et al. . | |
| 4,709,698 | 12/1987 | Johnston et al. . | |
| 4,719,914 | 1/1988 | Johnson . | |
| 4,753,223 | 6/1988 | Bremer . | |
| 4,765,331 | 8/1988 | Petruzzi et al. . | |
| 4,769,005 | 9/1988 | Ginsburg et al. . | |
| 4,774,949 | 10/1988 | Fogarty . | |
| 4,776,086 | 10/1988 | Kasevich et al. . | |
| 4,781,186 | 11/1988 | Simpson et al. . | |
| 4,784,638 | 11/1988 | Ghajar et al. . | |
| 4,785,829 | 11/1988 | Convert et al. . | |
| 4,798,215 | 1/1989 | Turner . | |
| 4,800,899 | 1/1989 | Elliott . | |
| 4,805,616 | 2/1989 | Pao . | |
| 4,813,429 | 3/1989 | Eshel et al. . | |
| 4,817,601 | 4/1989 | Roth et al. . | |
| 4,818,954 | 4/1989 | Flachenecker et al. . | |
| 4,822,333 | 4/1989 | Lavarenne . | |
| 4,823,791 | 4/1989 | D'Amelio et al. . | |
| 4,823,812 | 4/1989 | Eshel et al. . | |
| 4,860,744 | 8/1989 | Johnson et al. . | |
| 4,865,047 | 9/1989 | Chou et al. . | |
| 4,872,458 | 10/1989 | Kanehira et al. . | |
| 4,887,615 | 12/1989 | Taylor . | |
| 4,893,623 | 1/1990 | Rosenbluth . | |
| 4,896,671 | 1/1990 | Cunningham et al. . | |
| 4,898,577 | 2/1990 | Badger . | |
| 4,905,667 | 3/1990 | Foerster et al. . | |
| 4,906,230 | 3/1990 | Maloney et al. . | |
| 4,907,589 | 3/1990 | Cosman . | |
| 4,911,148 | 3/1990 | Sosnowski et al. . | |
| 4,911,173 | 3/1990 | Terwilliger . | |
| 4,919,129 | 4/1990 | Weber, Jr. et al. . | |
| 4,920,978 | 5/1990 | Colvin . | |
| 4,932,958 | 6/1990 | Reddy et al. . | |
| 4,936,281 | 6/1990 | Stasz . | |
| 4,940,064 | 7/1990 | Desai . | |
| 4,943,290 | 7/1990 | Rexroth | 606/49 |
| 4,946,449 | 8/1990 | Davis, Jr. . | |
| 4,949,706 | 8/1990 | Thon . | |
| 4,950,267 | 8/1990 | Ishihara et al. . | |
| 4,955,377 | 9/1990 | Lennox et al. . | |
| 4,961,435 | 10/1990 | Kitagawa et al. . | |
| 4,966,597 | 10/1990 | Cosman . | |
| 4,967,765 | 11/1990 | Turner et al. . | |
| 4,982,724 | 1/1991 | Saito et al. . | |
| 4,994,062 | 2/1991 | Nishigaki et al. . | |
| 4,998,932 | 3/1991 | Rosen et al. . | |
| 4,998,933 | 3/1991 | Eggers et al. . | |
| 5,002,558 | 3/1991 | Klein et al. . | |
| 5,003,991 | 4/1991 | Takayama et al. . | |
| 5,007,437 | 4/1991 | Sterzer . | |
| 5,007,908 | 4/1991 | Rydell . | |
| 5,010,886 | 4/1991 | Passafaro et al. . | |
| 5,026,959 | 6/1991 | Ito et al. . | |
| 5,029,588 | 7/1991 | Yock et al. . | |
| 5,030,227 | 7/1991 | Rosenbluth et al. . | |
| 5,035,695 | 7/1991 | Weber, Jr. et al. . | |
| 5,035,696 | 7/1991 | Rydell . | |
| 5,045,056 | 9/1991 | Behl . | |
| 5,045,072 | 9/1991 | Castillo . | |
| 5,055,109 | 10/1991 | Gould et al. . | |
| 5,057,105 | 10/1991 | Malone et al. . | |
| 5,057,106 | 10/1991 | Kasevich et al. . | |
| 5,057,107 | 10/1991 | Parins . | |
| 5,059,851 | 10/1991 | Corl et al. . | |
| 5,060,660 | 10/1991 | Gambale et al. . | |
| 5,071,418 | 12/1991 | Rosenbaum | 606/45 |
| 5,080,660 | 1/1992 | Buelna . | |
| 5,083,565 | 1/1992 | Parins . | |
| 5,084,044 | 1/1992 | Quint . | |
| 5,100,423 | 3/1992 | Fearnot . | |
| 5,108,415 | 4/1992 | Pinchuk et al. . | |
| 5,109,859 | 5/1992 | Jenkins . | |
| 5,116,615 | 5/1992 | Gokcen et al. . | |
| 5,120,316 | 6/1992 | Morales et al. . | |
| 5,122,137 | 6/1992 | Lennox | 606/42 |
| 5,135,525 | 8/1992 | Biscoping et al. . | |
| 5,150,717 | 9/1992 | Rosen et al. . | |
| 5,170,787 | 12/1992 | Lindegren . | |
| 5,178,620 | 1/1993 | Eggers et al. . | |
| 5,179,962 | 1/1993 | Dutcher et al. . | |
| 5,190,539 | 3/1993 | Fletcher et al. . | |
| 5,195,965 | 3/1993 | Shantha . | |
| 5,195,968 | 3/1993 | Lundquist et al. . | |
| 5,197,963 | 3/1993 | Parins | 606/41 |
| 5,201,732 | 4/1993 | Parins et al. . | |
| 5,207,672 | 5/1993 | Roth . | |
| 5,220,927 | 6/1993 | Astrahan et al. . | |
| 5,222,953 | 6/1993 | Dowlatshahi . | |
| 5,228,441 | 7/1993 | Lundquist . | |

| | | |
|---|---|---|
| 5,234,004 | 8/1993 | Hascoet et al. ............ 607/102 |
| 5,235,964 | 8/1993 | Abenaim . |
| 5,249,585 | 10/1993 | Turner et al. ............ 607/99 |
| 5,254,088 | 10/1993 | Lundquist et al. . |
| 5,257,451 | 11/1993 | Edwards et al. . |
| 5,273,524 | 12/1993 | Fox et al. . |
| 5,273,535 | 12/1993 | Edwards et al. . |
| 5,275,162 | 1/1994 | Edwards et al. . |
| 5,281,213 | 1/1994 | Milder et al. . |
| 5,281,217 | 1/1994 | Edwards et al. . |
| 5,281,218 | 1/1994 | Imran . |
| 5,287,845 | 2/1994 | Faul et al. . |
| 5,290,286 | 3/1994 | Parins . |
| 5,293,868 | 3/1994 | Nardella . |
| 5,293,869 | 3/1994 | Edwards et al. . |
| 5,299,559 | 4/1994 | Bruce et al. . |
| 5,300,068 | 4/1994 | Rosar et al. . |
| 5,300,069 | 4/1994 | Hunsberger et al. . |
| 5,300,070 | 4/1994 | Gentelia et al. . |
| 5,300,099 | 4/1994 | Rudie . |
| 5,301,687 | 4/1994 | Wong et al. . |
| 5,304,134 | 4/1994 | Kraus et al. . |
| 5,304,214 | 4/1994 | Deford . |
| 5,309,910 | 5/1994 | Edwards et al. . |
| 5,312,392 | 5/1994 | Hofstetter et al. . |
| 5,313,943 | 5/1994 | Houser et al. . |

FOREIGN PATENT DOCUMENTS

| | | |
|---|---|---|
| 9304727 | 4/1993 | WIPO . |
| 9308756 | 5/1993 | WIPO . |
| 9308755 | 5/1993 | WIPO . |
| 9320893 | 10/1993 | WIPO . |
| 9308757 | 10/1993 | WIPO . |
| 9320767 | 10/1993 | WIPO . |
| 9320768 | 10/1993 | WIPO . |
| 9320886 | 10/1993 | WIPO . |
| WO93/25136 | 12/1993 | WIPO . |
| 9403759 | 2/1994 | WIPO . |
| 9404222 | 3/1994 | WIPO . |
| 9405226 | 3/1994 | WIPO . |
| 9406377 | 3/1994 | WIPO . |
| 9407410 | 4/1994 | WIPO . |
| 9407411 | 4/1994 | WIPO . |
| 9407412 | 4/1994 | WIPO . |
| 9407413 | 4/1994 | WIPO . |
| 9407441 | 4/1994 | WIPO . |
| 9407446 | 4/1994 | WIPO . |
| 9407549 | 4/1994 | WIPO . |

OTHER PUBLICATIONS

Perinchery, Narayan, "Neoplasms of the Prostate Gland." pp. 378–409 (Date Unknown).

Urology 5th ed., Storz, Jan. 1992.

Transuretheral uwave Thermotherapy for Prostatism: Early Mayo Foundation Experience: Blute, Mayo Clinic Proceedings: vol. 67 May 92 p. 417–421.

New Therapies for Benign Prostatic Hyperplasia, Editorial Bruskewitz, Mayo Clinic Proceedings vol. 67 May 92 pp. 493–495.

Industry Strategies, Urology: "A Multi Billion Dollar Market. . ." Stephen Scala Nov. 19, 1991 pp. 1–32.

U.I. Dept. of Health and Human Services, MMWR 41: 401–404 vol. 41, No. 23, (Jun. 12, 1922).

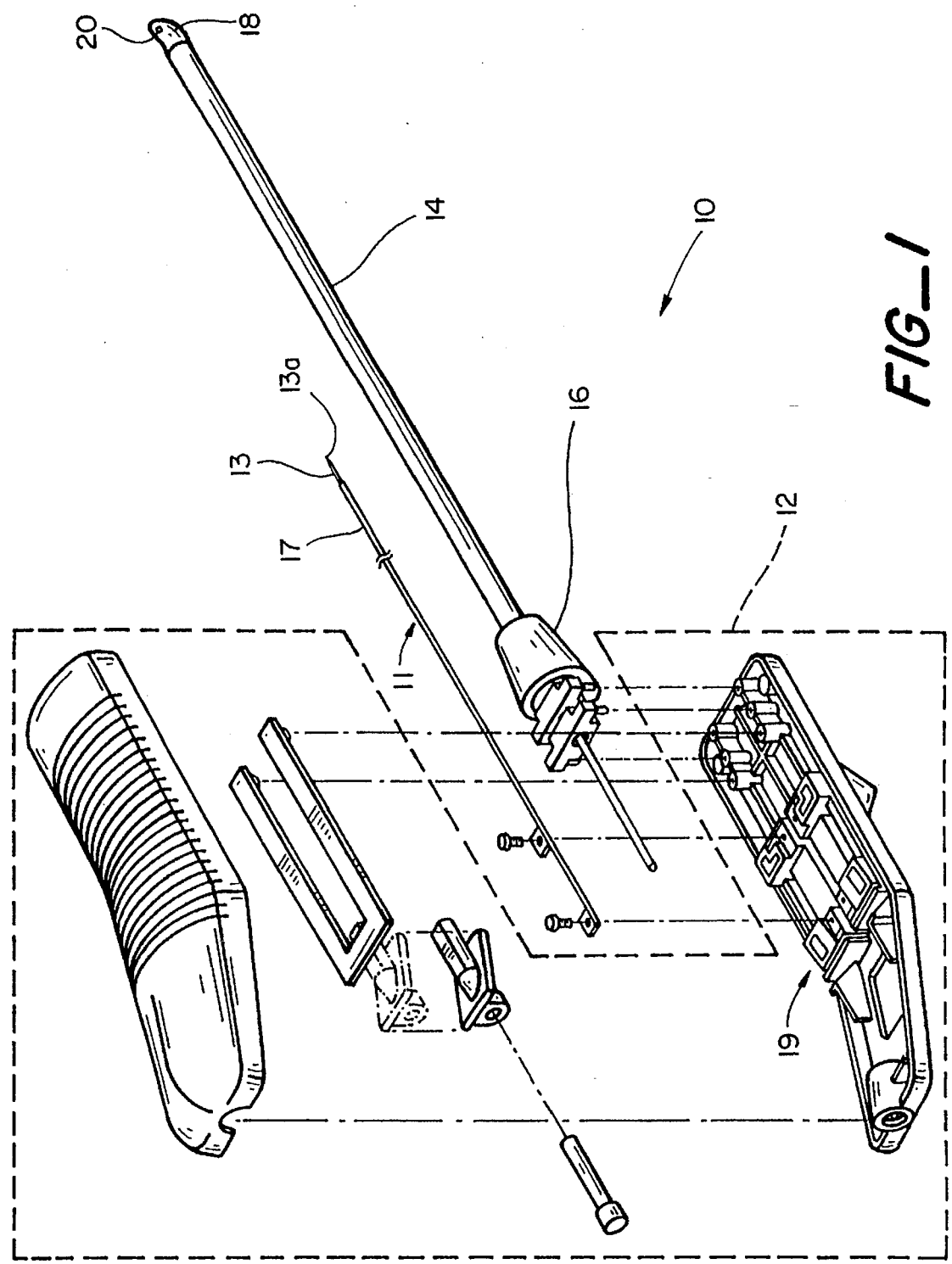
FIG_1

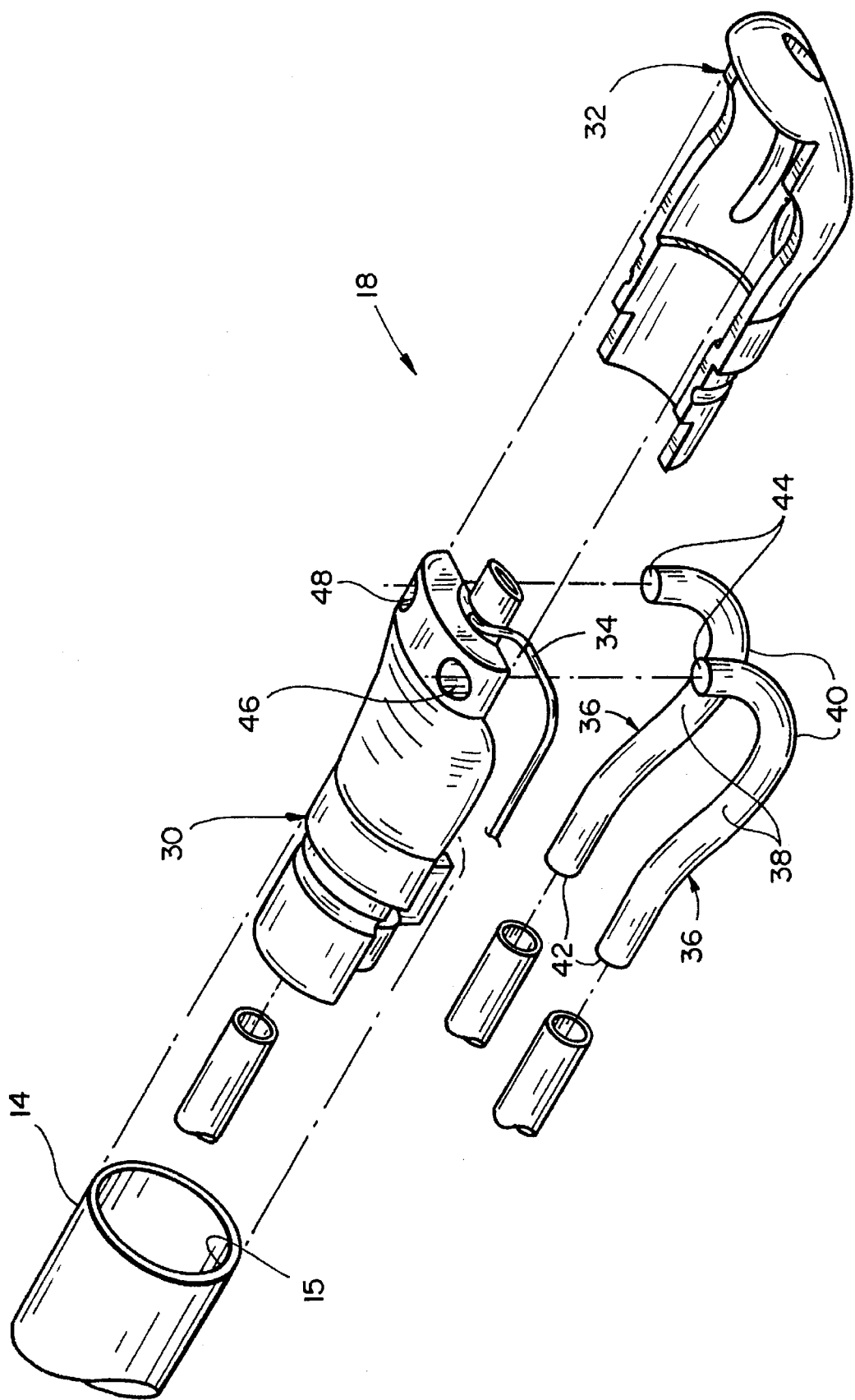

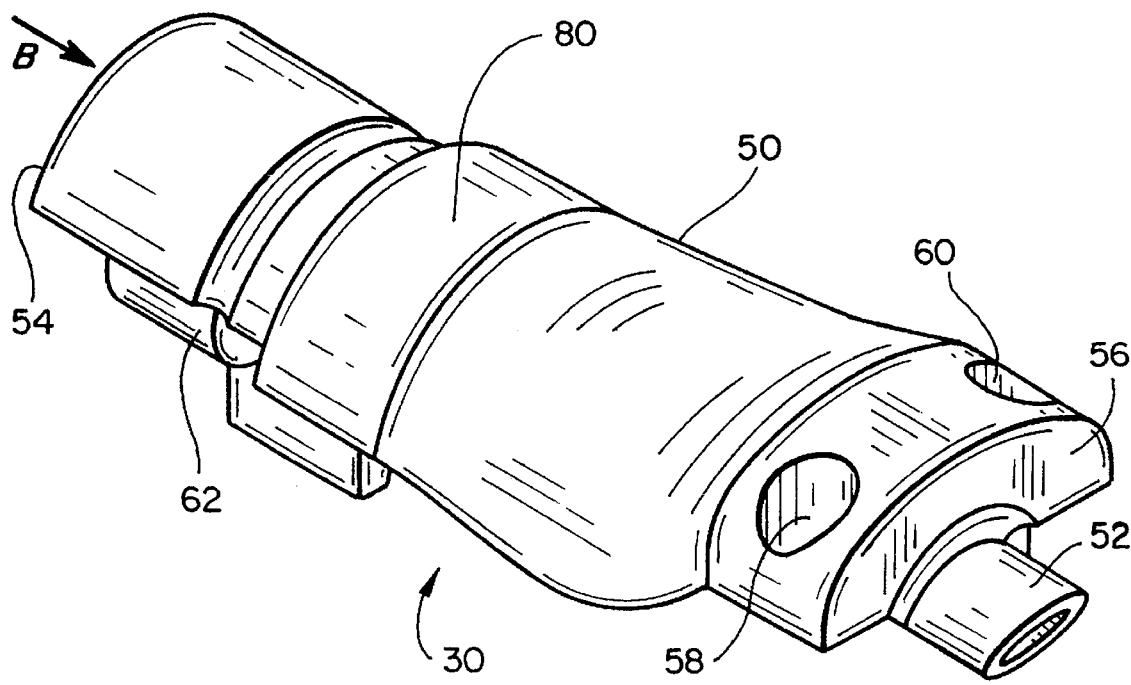
FIG_3
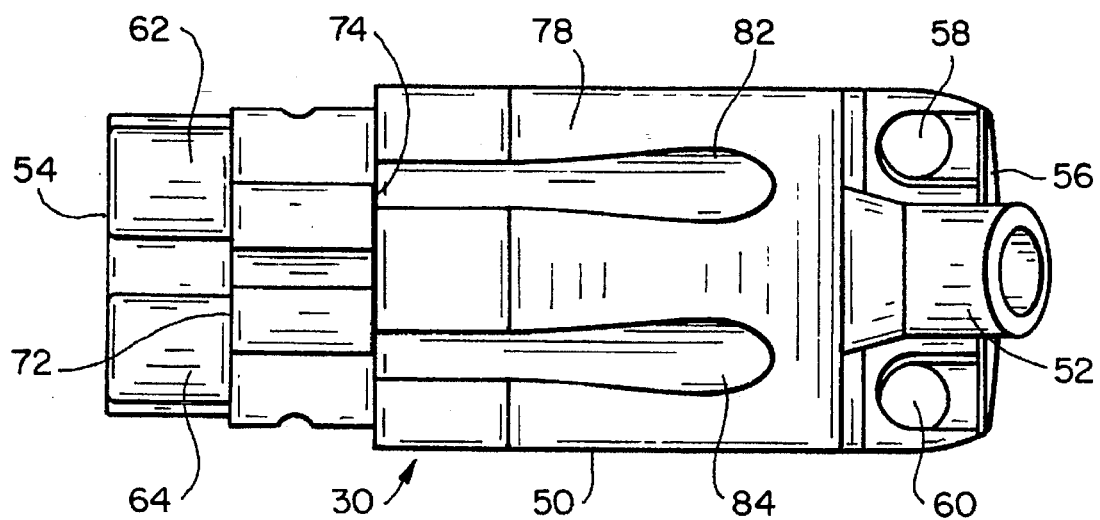
FIG_4

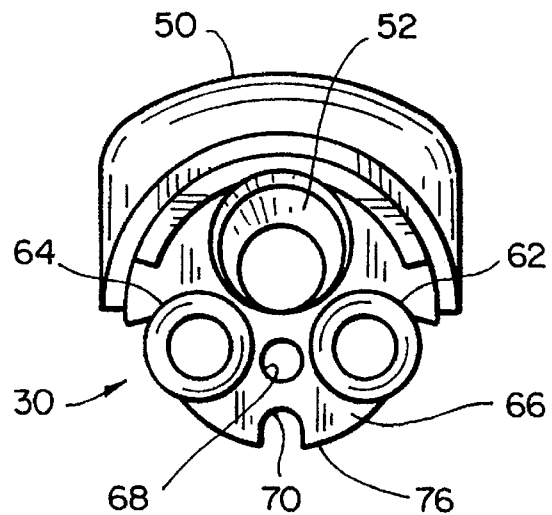
FIG_5
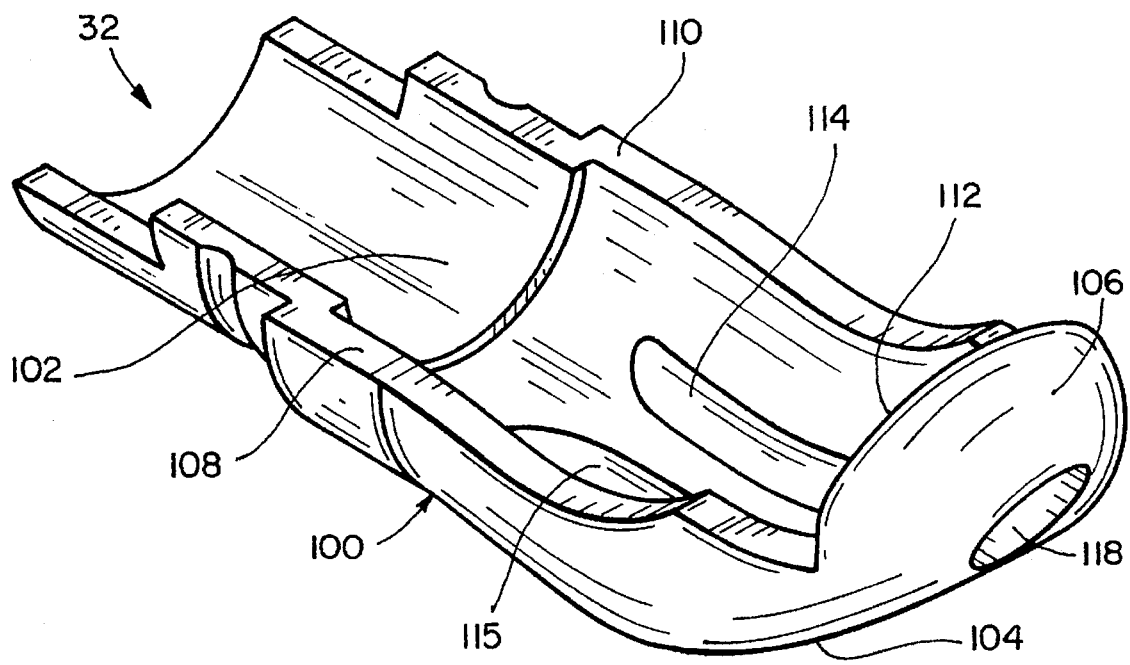
FIG_6

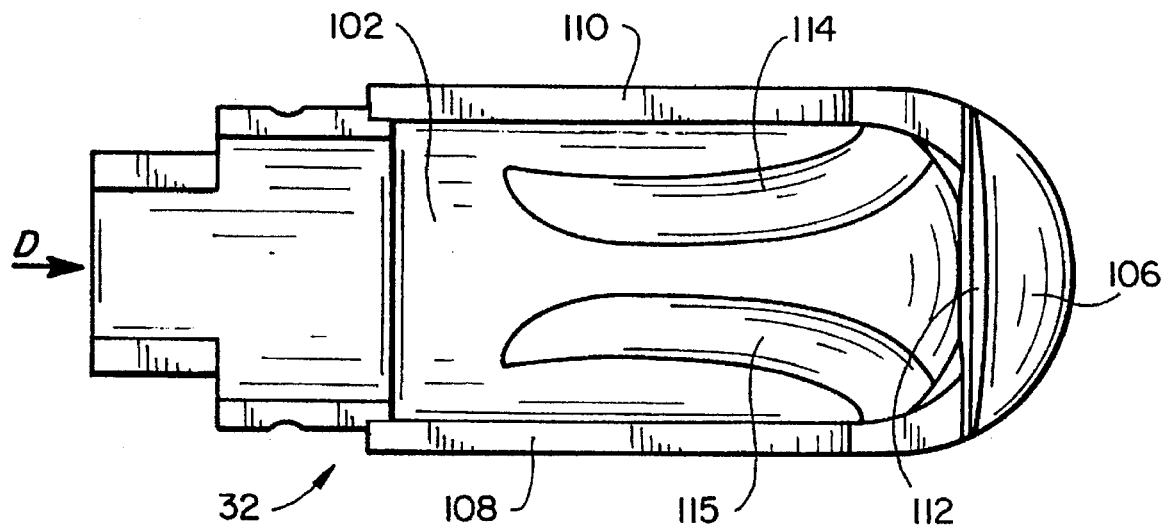
FIG_7
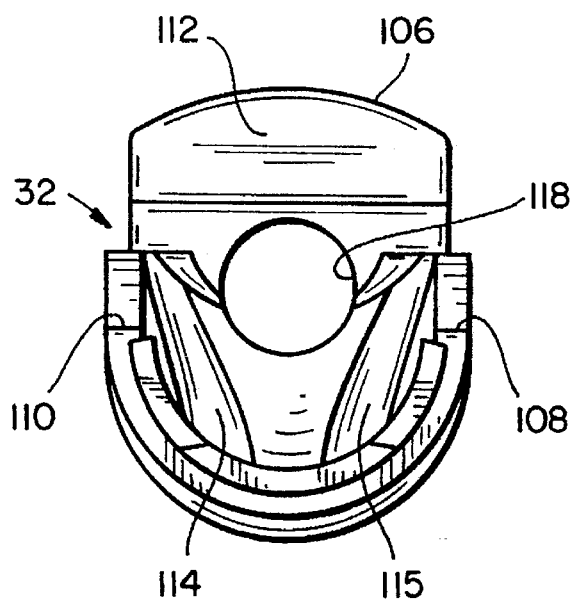
FIG_8

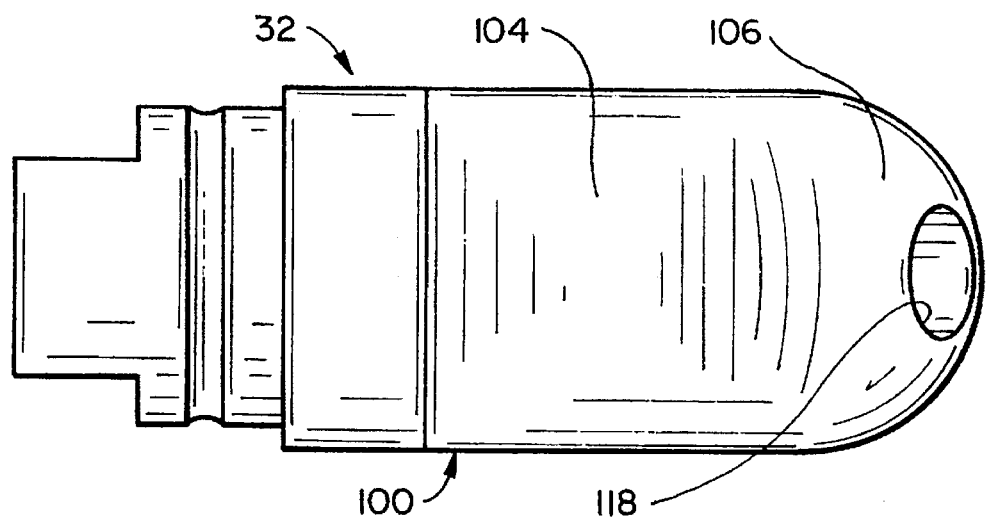
FIG_9
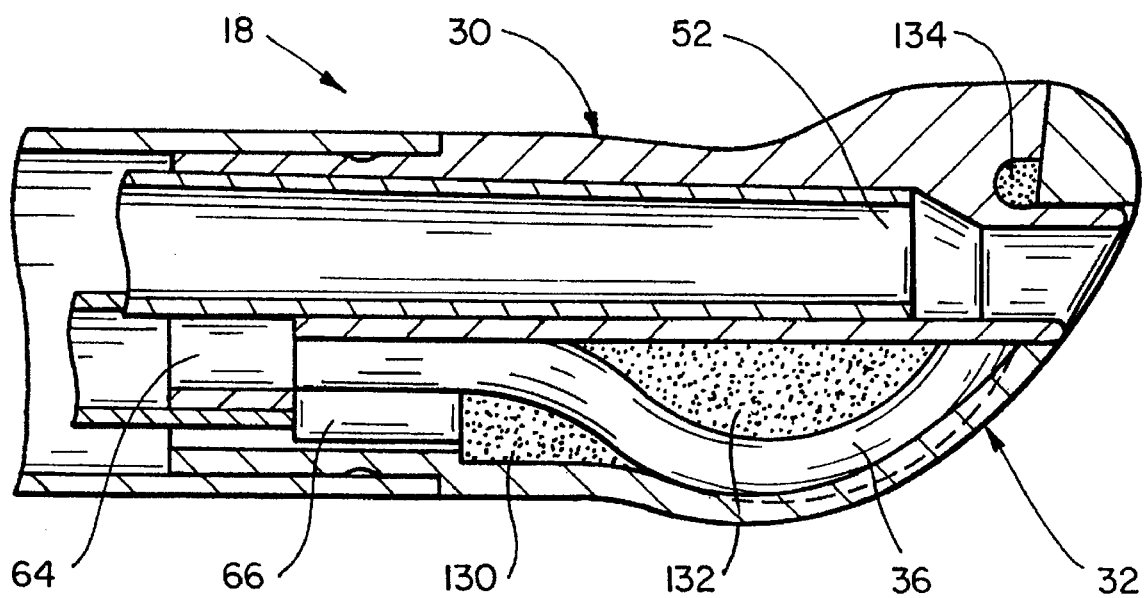
FIG_10

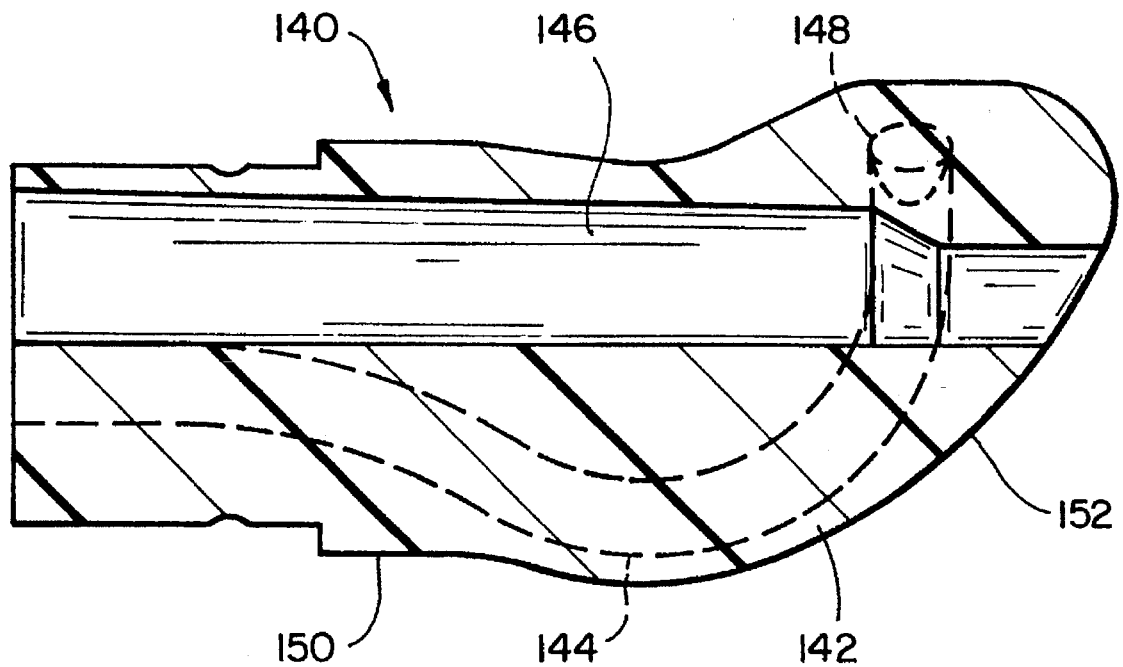
FIG_11
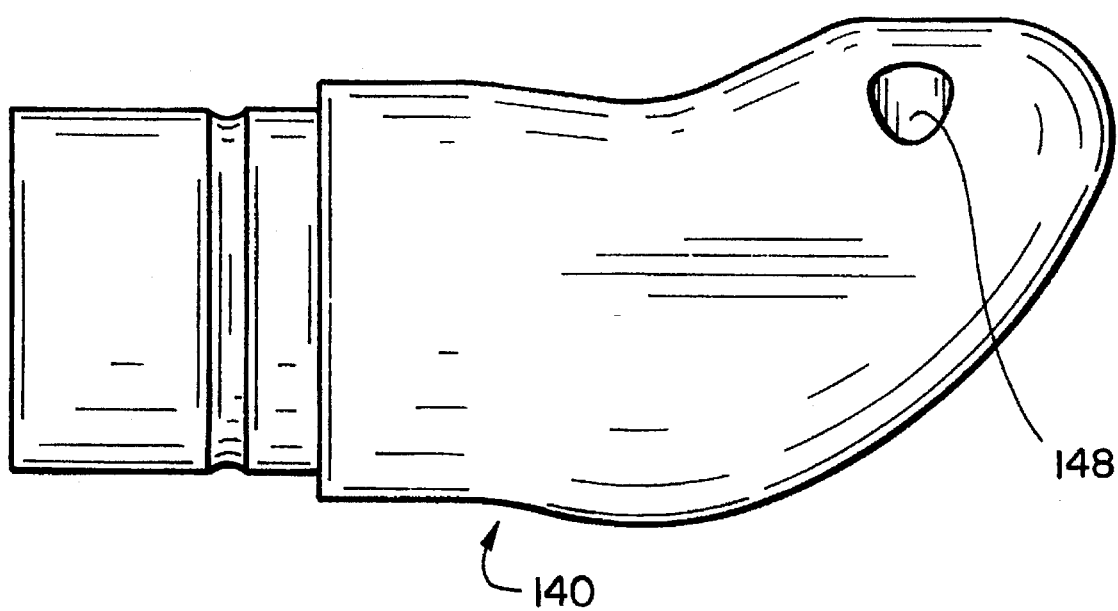
FIG_12

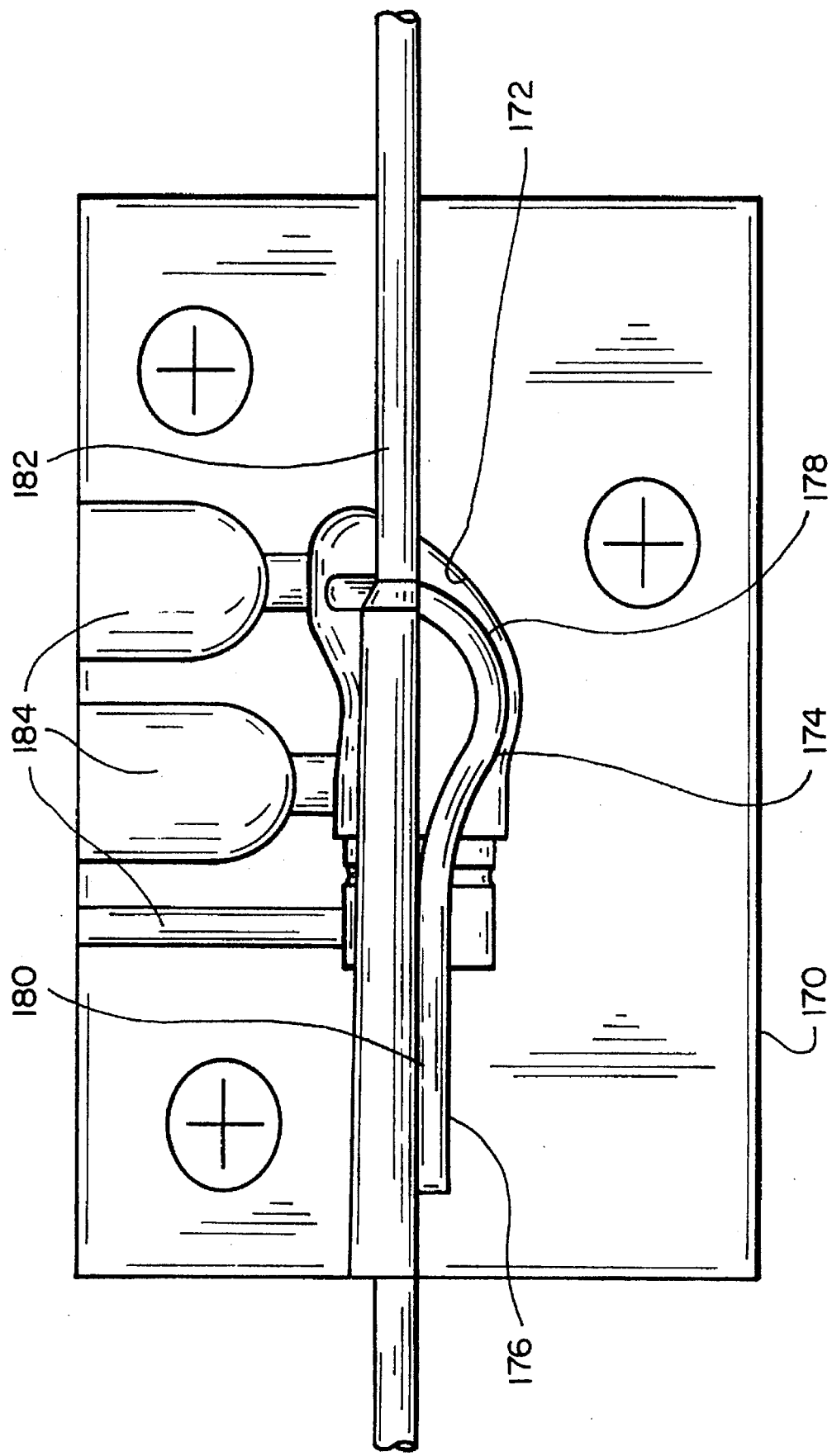
FIG_13

CATHETER TIP AND METHOD OF MANUFACTURING

RELATIONSHIP TO COPENDING APPLICATION

This application is a continuation-in-part of copending patent applications Ser. No. 07/929,638 filed Aug. 12, 1992, now abandoned, Ser. No. 08/012,370 filed Feb. 2, 1993 now U.S. Pat. No. 5,370,675, and Ser. No. 08/062,364 filed May 13, 1993 now U.S. Pat. No. 5,435,805.

FIELD OF THE INVENTION

This invention is directed to a unique device and method for penetrating body tissues for medical purposes such as tissue destruction and fluid substance delivery, for example. In particular, this invention is directed to a unique tip to be used with the above-mentioned device and the method of manufacturing the tip. The device penetrates tissue to the precise target selected in order to deliver energy to the tissue and/or deliver substances. It limits this activity to the precise preselected site, thereby minimizing trauma to normal surrounding tissue and achieving a greater medical benefit. This device is a catheter-like device for positioning a treatment assembly in the area or organ selected for medical treatment with at least one styler in the catheter, mounted for extension from a styler port in the side wall of the catheter through surrounding tissue to the tissue targeted for medical activity.

BACKGROUND OF THE INVENTION

Treatment of cellular tissues usually requires direct contact of target tissue with a medical instrument, usually by surgical procedures exposing both the target and intervening tissue to substantial trauma. Often, precise placement of a treatment probe is difficult because of the location of a target tissue in the body or the proximity of the target tissue to easily damaged, critical body organs, nerves, or other components.

Benign prostatic hypertrophy or hyperplasia (BPH), for example, is one of the most common medical problems experienced by middle to older aged men. Urinary tract obstruction due to prostatic hyperplasia has been recognized since the earliest days of medicine. Hyperplastic enlargement of the prostate gland often leads to compression of the urethra, resulting in obstruction of the urinary tract and the subsequent development of symptoms including frequent urination, decrease in urinary flow, nocturia, pain, discomfort, and embarrassment. The association of BPH with aging has been shown to exceed 50% in men over 50 years of age and increases in incidence to over 75% in men over 80 years of age. Symptoms of urinary obstruction occur most frequently between the ages of 65 and 70 when approximately 65% of men in this age group have prostatic enlargement.

Currently, there is no proven effective nonsurgical method of treatment of BPH. In addition, the surgical procedures available are not totally satisfactory. Currently, patients suffering from the obstructive symptoms of this disease are provided with few options: continue to cope with the symptoms (i.e., conservative management), submit to drug therapy at early stages, or submit to surgical intervention. More than 350,000 patients per year undergo surgery for removal of prostatic tissue in the United States.

Those suffering from BPH are often elderly men, many with additional health problems which increase the risk of surgical procedures. Surgical procedures for the removal of prostatic tissue are associated with a number of hazards including anesthesia associated morbidity, hemorrhage, coagulopathies, pulmonary emboli and electrolyte imbalances. These procedures performed currently can also lead to cardiac complications, bladder perforation, incontinence, infection, urethral or bladder neck stricture, retention of prostatic chips, retrograde ejaculation, and impotence. Due to the extensive invasive nature of the current treatment options for obstructive uropathy, the majority of patients delay definitive treatment of their condition. This circumstance can lead to serious damage to structures secondary to the obstructive lesion in the prostate (bladder hypertrophy, hydronephrosis, etc.) which is not without significant consequences. In addition, a significant number of patients with symptoms sufficiently severe to warrant surgical intervention are poor operative risks and are poor candidates for prostatectomy. In addition, younger men suffering from BPH who do not desire to risk complications such as impotence are often forced to avoid surgical intervention. Thus the need, importance and value of improved surgical and non-surgical methods for treating BPH is unquestionable.

High-frequency currents are used in electrocautery procedures for cutting human tissue especially when a bloodless incision is desired or when the operation site is not accessible with normal scalpel but presents an access for a thin instrument through natural body openings such as the esophagus, intestines or urethra. Examples include the removal of prostatic adenomas, bladder tumors or intestinal polyps. In such cases, the high-frequency current is fed by a surgical probe into the tissue to be cut. The resulting dissipated heat causes boiling and vaporization of the cell fluid at this point, whereupon the cell walls rupture and the tissue is separated. The frequency of the current for this use must be above ca. 300 khz in order to avoid any adverse such as nerve and/or muscle responses.

Destruction of cellular tissues in situ has been used in the treatment of many diseases and medical conditions alone or as an adjunct to surgical removal procedures. It is often less traumatic than surgical procedures and may be the only alternative where other procedures are unsafe. Ablative treatment devices have the advantage of using a destructive energy which is rapidly dissipated and reduced to a non-destructive level by conduction and convection forces of circulating fluids and other natural body processes.

Microwave, radiofrequency, acoustical (ultrasound) and light energy (laser) devices, and tissue destructive substances have been used to destroy malignant, benign and other types of cells and tissues from a wide variety of anatomic sites and organs. Tissues treated include isolated carcinoma masses and, more specifically, organs such as the prostate, glandular and stromal modules characteristic of benign prostate hyperplasia. These devices typically include a catheter or cannula which is used to carry a radiofrequency electrode or microwave antenna through a duct to the zone of treatment and apply energy diffusely through the duct wall into the surrounding tissue in all directions. Severe trauma is often sustained by the duct wall during this cellular destruction process, and some devices combine cooling systems with microwave antennas to reduce trauma to the ductal wall. For treating the prostate with these devices, for example, heat energy is delivered through the walls of the urethra into the surrounding prostate cells in an effort to kill the tissue constricting the urethra. Light energy, typically from a laser, is delivered to prostate tissue target sites by "burning through" the wall of the urethra. Healthy cells of the duct wall and healthy tissue between the modules and duct wall are also indiscriminately destroyed in the process and can cause unnecessary loss of some prostate function. Furthermore, the added cooling function of some microwave devices complicates the apparatus and requires that the device be sufficiently large to accommodate this cooling system.

OBJECTS AND SUMMARY OF THE INVENTION

The present invention is directed to a unique tip to be used with a medical device. The medical device is used to penetrate body cavities for medical purposes such as tissue destruction and fluid substance delivery.

The medical device of the present invention includes a control end and a probe end. The probe end comprises a tip which includes proximal and distal ends, a first shell, and a second shell which complementarily engages the first shell. The first shell has a first inside surface and the second shell has a second inside surface. The tip further includes at least one stylet port defined on its side and at least one stylet guide. The stylet guide engages the first and second inside surfaces. It extends from the proximal end of the tip and terminates at least one stylet port. The stylet guide comprises a first section having an axis parallel to a longitudinal axis of the tip, a second section having an axis at a predefined angle with the longitudinal axis and a curved section attached between the first and second section. The curved section extends to one side of the longitudinal axis. The tip may include an optical path which includes an optical lumen that extends from the proximal end to the distal end of the housing.

Accordingly, it is an objective of the present invention to provide a medical device that includes a unique tip.

It is another objective of the present invention to present a tip with a housing that includes two injection molded pieces that complementarily engage each other.

It is further an objective of the present invention to provide a tip that is cost effective and is easy to manufacture.

BRIEF DESCRIPTION OF THE DRAWINGS

FIG. 1 is an exploded, isometric view of a medical device using the styler guide of the present invention.

FIG. 2 is an exploded, isometric view of the first embodiment of stylet guide of the present invention.

FIG. 3 is an isometric view of the upper shell in FIG. 2.

FIG. 4 is a bottom view of the upper shell in FIG. 3.

FIG. 5 is an end view of the upper shell in FIG. 3, viewed in the direction of arrow B.

FIG. 6 is an isometric view of the lower shell in FIG. 2.

FIG. 7 is a top view of the lower shell shown in FIG. 6.

FIG. 8 is an end view of the lower shell shown in FIG. 6, viewed in the direction of arrow D in FIG. 7.

FIG. 9 is an bottom view of the lower shell shown in FIG. 6.

FIG. 10 is a cross-sectional side view of an assembled stylet guide of FIG. 2.

FIG. 11 is a cross-sectional side view of a second embodiment of the stylet guide of this invention.

FIG. 12 is a side view of the stylet guide of FIG. 11.

FIG. 13 is the side view of a mold half used to fabricate the stylet guide of FIG. 11.

DETAILED DESCRIPTION OF THE INVENTION

The device of this invention provides a precise, controlled positioning of a treatment stylet in a tissue targeted for treatment, destruction or sampling from a catheter positioned in the vicinity of the target tissue. This is described in application Ser. Nos. 07/929,638 and 08/012,370, the entire contents of which are incorporated herein by reference. In this process, it utilizes a unique tip portion which is presented in this application, The term "styler" as used hereinafter is defined to include both solid and hollow probes which are adapted to be passed from a catheter port through normal tissue to a target tissue. The styler is shaped to facilitate easy passage through tissue. It can be a solid wire, thin rod, or other solid shape or it can be a thin hollow tube or other shape having a longitudinal lumen for housing a thermocouple or for introducing fluids to or removing materials from a site. The styler preferably has a sharpened end to reduce resistance and trauma when it is pushed through tissue to a target site.

The styler can be designed to provide a variety of medically desired treatments of a selected tissue. As a radiofrequency electrode or microwave antenna, it can be used to ablate or destroy the target tissue. As a hollow tube, it can be used to deliver a treatment fluid such as a liquid to a target tissue. The liquid can be a simple solution or a suspension of solids, for example, colloidal particles, in a liquid. Since the styler is very thin, it can be directed from the catheter through intervening normal tissue with a minimum of trauma to the normal tissue.

The device and method of this invention provide a more precise, controlled medical treatment which is suitable for destroying cells of medically targeted tissues throughout the body, both within and external to body organs. The device and method are particularly useful for treating benign prostate hyperplasia (BPH), and the device and its use are hereinafter described with respect to BPH, for purposes of simplifying the description thereof. It will be readily apparent to a person skilled in the art that the device and method can be used to destroy body tissues in any body cavities or tissue locations that are accessible by percutaneous or endoscopic catheters, and is not limited to the prostate. Application of the device and method in all of these organs and tissues is intended to be included within the scope of this invention.

BPH is a condition which arises from the benign replication and growth of cells in the prostate, forming glandular and stromal nodules which expand the prostate and constrict the opening of the prostatic urethra. Glandular nodules are primarily concentrated within the transition zone, and stromal nodules within the periurethral region. Traditional treatments of this condition have included surgical removal of the entire prostate gland, digital removal of the adenoma, as well as transurethral resection of the urethral canal and prostate to remove tissue and widen the passageway. One significant and serious complication associated with the latter method is iatrogenic sterility. More recently, laser treatment has been employed to remove tissue, limiting bleeding and loss of body fluids.

Microwave therapy has been provided with some success by positioning a microwave antenna within the prostatic urethra and generating heat in the tissue surrounding the urethra with a microwave field. Coolants are sometimes applied within the catheter shaft to reduce the temperature of the urethral wall. This necessitates complicated mechanisms to provide both cooling of the immediately adjacent tissues while generating heat in the more distant prostatic tissue. This technique is similar to microwave hyperthermia. Similarly, radiofrequency tissue destruction with electrodes positioned within the urethra has limited applicability since it necessarily exposes the urethral wall to destructive temperatures. To avoid this, low temperature settings required to protect the urethra must be so low that the treatment time required to produce any useful effect is unduly extended, e.g. up to three hours of energy application.

One embodiment of the device of this invention uses the urethra to access the prostrate and positions RF electrode stylets directly into the tissues or nodules to be destroyed. The portion of the stylet conductor extending from the urethra to the target tissue is enclosed within a longitudinally adjustable sleeve shield which prevents exposure of the tissue adjacent to the sleeve to the RF current. Thus, the ablative destruction is confined to the tissues targeted for destruction, namely those causing the constriction. The catheter includes one or more inflatable annular balloons for exerting an outward force on surrounding tissue. This allows the body canal, for example the urethra, along which the catheter is introduced to be widened. In this way immediate short-term relief may be provided to constricted passageways. In contrast, the ablation of tissue surrounding the canal or passageway provides for long-term relief, the effect of which typically takes effect only once the destroyed tissue cells have been removed by the natural body processes. Other aspects of the invention will become apparent from the drawings and accompanying descriptions of the device and method of this invention. It will be readily apparent to a person skilled in the art that this procedure can be used in many areas of the body for percutaneous approaches and approaches through body canals.

FIG. 1 shows the medical device 10 using the stylet guide of the present invention. Device 10 includes catheter 14 which has a passageway 15 extending therethrough and is connected to the control unit 12 by means of a connector 16. Tip 18 is connected to the distal end of the catheter 14. Tip or stylet guide housing 18 includes at least one stylet port 20 which allows a flexible to protrude and contact the target issue. Stylet 11 includes a conductive radio frequency electrode 13 with a sharpened tip 13a and an insulating sleeve 17 slidably mounted on electrode 13. Means 19 is carried by control unit 12 and is connected to electrode 13 and insulating sleeve 17 for causing advancement of stylet 11 through passageway 15. The following presents the description of different embodiments of tip 18.

FIG. 2 is an isometric view of the first embodiment of tip 18. Tip 18 includes a first or upper shell 30, a second or lower shell 32 which complimentarily engages upper shell 30, a thermocouple 34, and a pair of stylet guides 36. Each one of stylet guides or tubular member 36 have inside surface 38, outside surface 40, proximal end 42, and distal end 44. Tip 18 further includes a pair of stylet ports 46 and 48 which are provided in upper shell 30. The method of interconnecting the above components will be described in conjunction with FIG. 10.

FIGS. 3–5 are different views of upper shell 30. FIG. 3 is an isometric view of upper shell 30, FIG. 4 is a bottom view of upper shell 30 in FIG. 3, and FIG. 5 is an end view of upper shell 30 in FIG. 3.

As can be seen in FIGS. 3 and 5, upper shell 30 includes a body 50 and longitudinal tube 52 which extends from the proximal end 54 to the distal end 56 and protrudes out of distal end 56. FIG. 5 shows that diameter of longitudinal tube 52 tapers off as it nears distal end 56. Body 50 includes two styler ports 58 and 60 which are situated near the distal end on either sides of longitudinal axis of body 50.

FIGS. 4 and 5 further show that upper shell 30 includes a pair of tube sections 62 and 64 which are situated near proximal end 54 on either sides of the longitudinal axis of body 50. FIG. 4 further shows a pair of inside surfaces or channel sections 82 and 84 which engage inside surfaces 38 of stylet guides 36 when tip 18 is assembled. FIG. 5 shows that upper shell 30 further includes H-shaped section 66 which includes a hole 68 extending from its end 72 to end 74. H-shaped section 66 further includes a semi-circular recess 70 which is provided on bottom circular surface 76 of H-shaped section 66. Recess 70 extends from end 72 to end 74.

Longitudinal tube 52 is positioned between inside surface 78 and outside surface 80 of body 50. Longitudinal tube 52 provides a lumen for optical means to be extended through tip 18. Each of the tube sections 62 and 64 receives one end of a respective stylet guide 36. The other ends of the guide tubes 36 fit in stylet ports 58 and 60, respectively. Ports 58 and 60 allow flexible stylets 11 to protrude out of tip 18 (FIG. 1) and contact the selected tissue. Either hole 68 or recess 70 can be used to extend the thermal couple 34 (FIG. 2) though tip 18 (FIG. 1). In the case that one is used to extend the thermocouple 34, the other is used to inject adhesive material into the gaps found inside tip 18 after assembly. This process will fully be explained with respect to FIG. 10. By engaging inside surface 38 of guide tube 36, channel sections 82 and 84 ensure that stylet guides 36 are properly positioned inside tip 18 to guide the flexible tubes. As will be presented below, outside surfaces 40 of stylet guides 36 engage inside surfaces or channel sections 114 and 115 of lower shell 32.

Each guide tube 36 provides a path for a respective flexible styler to be guided out of the catheter 14 (FIG. 1) through a respective stylet port. As disclosed in the above-identified co-pending applications, a typical flexible styler has a puncturing tip. Accordingly, stylet guides 36 must be made of a material which is sufficiently hard to prevent the puncturing tip from deforming and snagging on the tube surface as the stylets are being extended distally. In the present invention, the stylet guides are preferably made of metal, such as stainless steel, for example.

Although, stylet guides are used to guide the flexible stylets 11 through tip 18, this is not to be a limiting factor. It is perfectly within the scope of the present invention to use other guiding formations which are capable of performing like the stylet guides. These formations would be readily apparent to a person skilled in the art in view of the structure of the stylet guides 36.

FIGS. 6–9 are different views of lower shell 32 shown in FIG. 2. FIG. 6 is an isometric view of lower shell 32. FIG. 7 is a top view, FIG. 8 is an end view and FIG. 9 is a bottom view of the shell of FIG. 6.

As can be seen if FIGS. 6–9, lower shell 32 includes a body 100 which has an inside surface 102, an outside surface 104, and an extended section 106. Lower shell 32 includes mating surfaces 108, 110 and 112 which mate with the opposed surfaces of upper shell 30. Lower shell 32 further includes two inside surfaces 114 and 115 and an opening 118. Inside surfaces 114 and 116 are provided on the inside surface 102 of lower shell and extend from approximately the middle of the length of lower shell 32 to the beginning of extended section 106.

Inside surfaces 114 and 116 are situated on opposite sides of the longitudinal axis of lower shell 32. They begin with an orientation parallel to the longitudinal axis and end with an orientation at an angle to the longitudinal axis. Inside surfaces 114 and 116 mate with outside surfaces 40 of stylet guides 36 shown in FIG. 2. Inside surfaces 114 and 116 further provide the means to maintain stylet guides 36 in position when tip 18 is assembled. Opening 118 is provided to allow the extension of longitudinal tube 52 (FIG. 5) through the distal tip when upper shell 30 and lower shell 32 are assembled together.

Both upper shell 30 and lower shell 32 are manufactured by injection molding. The mold is manufactured using conventional precision milling equipment. Once the injected plastic has solidified, the part is removed from the mold. The material used to manufacture the two shells can be a polycarbonate or equivalent injection molding plastic.

The following steps are followed to assemble the tip 18 of FIG. 2. Proximal ends 42 of stylet guides 36 are inserted into distal ends of tube sections 62 and 64, respectively. Distal end 44 of guide tube 36 is inserted in stylet ports 58 and 60. Next, upper shell 30 and lower shell 32 are joined together such that mating surfaces 108, 110 and 112 of lower shell 32 mate with the opposed surfaces of the upper shell 30. At this point, inside surfaces 82, 84, 114 and 115 engage their respective opposing surfaces on stylet guides 36 to ensure that stylet guides 36 are properly positioned within tip 18. Then, adhesive material, such as epoxy resin, is injected through hole 68 or recess 70 to fill spaces 130, 132 and 134 (See FIG. 10) left in the above assembly. The cured adhesive secures the stylet guides 36 in position.

Finally, the abutting surfaces of upper and lower shells 30 and 32 can be sealed by ultrasonic welding or a conventional adhesive.

FIG. 10 is a side view of an assembled tip 18 according to the method presented above. FIG. 10 shows upper shell 30, lower shell 32, longitudinal tube 52 (FIG. 3), one guide tube 36, tube section 64, and H-shaped section 66. It further shows spaces 130, 132 and 134 which are filed with adhesive material before sealing the abutting surfaces.

Although tip 18 of FIG. 2 includes two stylet guides 36 and two stylet ports 46 and 48, tip 18 could also have one guide tube 36 with one corresponding stylet port or more than two stylet guides 36 with corresponding styler ports. Obviously, the numbers of stylet ports directly correspond to the number of stylet guides. Ultimately, the number of stylet guides is determined by the number of flexible stylets used in medical device 10.

FIG. 11 is a side view of a second embodiment of tip 18 (FIG. 1). Tip 140 includes a housing 142, a guide tube 144, a longitudinal tube 146, and a stylet port 148. Housing 142 has a horizontal portion 150 and an angled portion 152, as the extension of the horizontal portion 150. Housing 142 is a single piece body and is manufactured using a mold. Details of the method of manufacturing tip 140 will be presented later.

Guide tube 144 provides the same function as stylet guides 36. It provides a path for stylet to be guided out of the catheter 14 (FIG. 1) through stylet port 148. It too must be made of hard enough material to prevent any damage to its inside surfaces due to the puncturing tip of the flexible stylet. In the present invention, it is preferably made of metal, such as stainless steel.

Longitudinal tube 146 provides a passage way for an optical probe to be extended all the way near or by the extreme distal point of the tip 140. A catheter with optical means is presented in a co-pending application Ser. No. 08/062,364, filed on May 13, 1993, the entire content of which is incorporated by reference. Similar to longitudinal tube 52 of tip 18 in FIGS. 2, the diameter of longitudinal tube 146 tapers toward the distal end of tip 140.

Similar to tip 18 of FIG. 2, tip 140 could also have a lumen (not shown) that provides a path for a thermocouple probe to be extended all the way near the distal end of tip 140. This probe provides the capability of measuring the temperature of the tissues in the vicinity of the target tissue. This allows the operator to monitor the temperature of this region and prevent this temperature to exceed the acceptable level.

Depending on the requirement of the catheter, stylet port 148 could be placed at different angles with respect to the longitudinal axis of tip 140. For example, stylet port 148 can be placed at a 90° angle with respect to the longitudinal axis of tip 140 as shown in FIG. 12.

Although one guide tube 144 and one stylet port 148 is shown in tip 140 of FIG. 11, tip 140 may have more than one stylet guides 144 and corresponding stylet ports 148. The number of stylet guides 144 corresponds to the number of stylet ports 148. For example, tip 140 could have two stylet guides 144 and two corresponding stylet ports 148.

The present invention utilizes a mold to fabricate tip 140. FIG. 13 is the side view of a mold 170 used to fabricate tip 18. Mold 170 includes two pieces (not shown). Each piece includes a cavity formed in approximately its middle section which corresponding to half of housing 142. Upon joining the two halves, a cavity 172 defining the perimeter of housing 142 is created in the middle of mold 170. Mold 170 includes a pathway 174 to house a bent tube 176. Bent tube 176 has two sections; a curved section 178 and a straight section 180. Straight section 180 extends out of the proximal end of cavity 172. Once the casting material is introduced inside cavity 172 and it is hardened, the resulting tip would have a part of straight section 180 protruding out of its proximal end. This section is then removed by cutting it. The remaining part of bent tube 176 forms guide tube 144.

Mold 170 further includes a lumen to receive an optic pin 182. Once the cast tip 140 is manufactured according to the process which will be hereinafter explained, the optic pin 182 is removed. The remaining lumen forms the longitudinal tube 146.

Mold 170 further includes apertures 184 through which a casting resin is introduced into the cavity 172. Although mold 170 is shown to have a path for one bent guide tube, paths for two or more guide tubes can also be provided. In this case, the corresponding increase in number of stylet ports 148 is provided.

In the casting process, the inner surfaces of each mold half. Thereafter, mold release is applied to the inside surfaces. Bent tube 176 is positioned in place. Thereafter, optic pin 182 is positioned. Next, the two pieces of mold 170 are assembled together. Then, casting resin is introduced into cavity 172 through apertures 184. The material solidifies or cures to form to tip. Optic pin 182 is then removed from housing 142.

As mentioned before, the catheter may have a thermocouple probe to monitor the temperature of the tissues in the vicinity of the target tissue. To provide for this embodiment, a thermocouple lumen (not shown) is provided in the mold housing. The thermocouple is placed in the lumen before introducing the casting material into cavity 172. Preferably, the thermocouple is encased in a shrinkable plastic tube and heat is used to shrink the tube. The tube protects the thermocouple tube and maintains it in position.

Both tip 18 and 140, presented above, attach to the distal end of catheter 14. They both provide a means to guide a flexible styler 11 out of catheter 14 through stylet ports.

As mentioned above, stylet guides 36 and 144 include a straight section which is parallel to the longitudinal axis of tips 18 or 140, respectively, and a curved section. The curved section of both stylet guides bents to one side of the longitudinal axis and extends to the corresponding stylet port by crossing the longitudinal axis at a specified angle. The crossing angle determines the angle that the corresponding stylet port makes with the longitudinal axis. The crossing angle also determines the angle by which the flexible stylet protrudes out of the tip. For example, in FIG. 2 or 10, guide tube 36 bends below the longitudinal axis of tip 18 and crosses back at a right angle. Accordingly, the stylets 11 out of stylet guides 36 exit tip 18 at a 90° angle with respect to the longitudinal axis of tip 18.

The above mechanism provides the capability of extending the flexible stylets 11 further inside the walls of the cavity, such as urethra, that its being inserted in. This enables the present invention to reach the target tissue which are further behind the walls of the cavity.

Furthermore, the above mechanism provides the capability of extending the flexible stylets 11 out of the catheter at different desired angles without a need for sharp bends at the distal end of the flexible stylets. The present catheters require short bend at the distal end of stylets 11.

Thus, a stylet guide and the method of production of such according to the present invention has been described with respect to specific embodiments. Other variations of the present invention are obvious to one knowledgeable in the art. For example, other lumens could be provided within the housing of stylet guide of the present invention for other purposes. Therefore, the present invention is not to be limited except by the appended claims.

We claim:

1. A medical device comprising an elongate probe member having proximal and distal extremities and having a passageway therein extending from the proximal extremity to the distal extremity along a longitudinal axis, a stylet mounted in the elongate probe member and having proximal and distal extremities, control means mounted on the proximal extremity of the elongate probe member, means mounted on the proximal extremity of the elongate probe member and connected to the control means and connected to the stylet for causing advancement of the stylet through the passageway, a stylet guide housing mounted on the distal extremity of the elongate probe member and having an outer surface with a port therein, a tubular member defining a lumen in communication with the passageway and extending through the stylet guide housing in a curved path to the port for slidably receiving the stylet and causing the distal extremity of the stylet to be advanced from the stylet guide housing sidewise at an angle with respect to the longitudinal axis.

2. A device of claim 1 wherein the stylet guide housing includes a first section having an axis parallel to a longitudinal axis of the tip, a second section having an axis at a predefined angle with the longitudinal axis, and a curved section extending to one side of the longitudinal axis and attached between the first and second section.

3. A device of claim 1 wherein the stylet guide housing is further provided with an optical lumen extending along the longitudinal axis.

4. A device of claim 3 wherein the optical lumen tapers as it extends distally.

5. A device of claim 1 together with a temperature sensor carried within the stylet guide housing.

6. A device of claim 1 wherein the stylet guide housing is made from a plastic having a hardness and the tubular member is made from a material having a hardness which is greater than the hardness of the plastic.

7. A device of claim 6 wherein the tubular member is made from metal.

8. A device of claim 7 wherein the tubular member is made from stainless steel.

9. A device of claim 6 wherein the stylet guide housing is made from injection molded polycarbonate.

10. A device of claim 1 wherein the stylet includes a conductive radio frequency electrode with a sharpened tip and an insulating sleeve coaxially mounted on the conductive radio frequency electrode.

11. A device of claim 10 wherein the insulating sleeve is slidably mounted on the conductive radio frequency electrode.

12. A device of claim 1 wherein the stylet guide housing has a rounded distal end.

13. A device of claim 12 wherein the stylet guide housing is bullet-shaped.

14. A medical probe device having a catheter comprising:
a control end and a probe end, the probe end comprising a tip including proximal and distal ends; a first shell having a first inside surface; a second shell complementarily engaging the first shell and having a second inside surface; at least one stylet port defined on a side thereof; and at least one stylet guide engaging said first and second surfaces and extending from the proximal end of the tip and terminating at said at least one stylet port, the stylet guide comprising a tube extending from the proximal end of the tip to the at least one stylet port.

15. A device of claim 14 wherein said first shell comprises proximal and distal ends and inside and outside surfaces; at least one first tube section attached to its inside surface and extending from the proximal end to a first point between the proximal and distal ends; means defining a second tube section attached to the inside surface of the second shell, said means extending from the first point to a second point between the proximal and distal ends of the first shell; and a third tube positioned between the inside and outside surfaces, the third tube being parallel to the longitudinal axis of the first shell and extending from the proximal end to a point adjacent the distal end of the second shell.

16. A device of claim 15 wherein the third tube defines an optical lumen.

17. A device of claim 15 further comprising a temperature sensing probe extending through the second tube section and terminating near the distal end of the first shell.

18. A stylet guide housing for use with a catheter shaft having proximal and distal extremities and a passageway therein extending from the proximal extremity to the distal extremity along a longitudinal axis, a stylet slidably mounted in the passageway of the catheter shaft and having proximal and distal extremities, comprising a body having proximal and distal end portions and a smooth outer surface with a port therein, means carried by the proximal end portion adapted for mounting the body on the distal extremity of the catheter shaft, a tubular member defining a lumen in communication with the passageway and extending through the stylet guide housing in a curved path to the port for slidably receiving the stylet and causing the distal extremity of the stylet to be advanced from the stylet guide housing sidewise at an angle with respect to the longitudinal axis, the tubular member being made from metal for facilitating advancement of the stylet through the curved path.

19. A device of claim 18 wherein the tubular member includes a first section having an axis parallel to a longitudinal axis of the tip; a second section having an axis at a predefined angle with the longitudinal axis; and a curved section extending to one side of the longitudinal axis and attached between the first and second sections.

20. A device of claim 18 wherein the body is provided with an optical lumen extending therethrough.

21. A device of claim 17 wherein the optical lumen extends between the proximal and distal end portions of the body.

22. A device of claim 21 wherein the optical lumen tapers as it extends distally.

23. A device of claim 18 together with a temperature sensor carried by the body.

24. A device of claim 18 wherein the body is made from injection molded plastic.

25. A device of claim 18 wherein the body has a rounded distal end.

26. A medical probe device having a catheter including a control end and a probe end, the probe end comprising a tip including proximal and distal ends; a first shell having a first inside surface; a second shell complementarily engaging the first shell and having a second inside surface; at least one stylet port defined on a side thereof; and stylet guide means for guiding a flexible stylet outwardly through the tip and through the at least one stylet port and intervening tissues to target tissues, the stylet guide means engaging said first and second surfaces and comprising a tube extending from the proximal end of the tip to the at least one stylet port.

\* \* \* \* \*

UNITED STATES PATENT AND TRADEMARK OFFICE
CERTIFICATE OF CORRECTION

PATENT NO. : 5,630,794

DATED : May 20, 1997

INVENTOR(S) : Ronald G. LAX; James A. BAKER

It is certified that error appears in the above-indentified patent and that said Letters Patent is hereby corrected as shown below:

Title page, item [54] and Col. 1:
Change title from "CATHETER TIP AND METHOD OF MANUFACTURING" to --MEDICAL PROBE DEVICE AND CATHETER TIP FOR USE THEREWITH--.

| Column | Line | |
|--------|------|---|
| 1 | 26 | change "styler" to --stylet-- |
| 1 | 27 | change "styler" to --stylet-- |
| 3 | 44 | change "styler" to --stylet-- |
| 4 | 11 | change "styler" to --stylet-- |
| 4 | 14 | change "styler" to --stylet-- |
| 4 | 18 | change "styler" to --stylet-- |
| 4 | 21 | change "styler" to --stylet-- |
| 4 | 28 | change "styler" to --stylet-- |
| 5 | 40 | after "flexible" insert --stylet 11-- |

UNITED STATES PATENT AND TRADEMARK OFFICE
CERTIFICATE OF CORRECTION

PATENT NO. : 5,630,794
DATED : May 20, 1997
INVENTOR(S) : Ronald G. LAX; James A. BAKER It is certified that error appears in the above-indentified patent and that said Letters Patent is hereby corrected as shown below:

| Column | Line | |
|---|---|---|
| 5 | 52 | change "member " to --members-- |
| 6 | 01 | change "styler" to --stylet-- |
| 6 | 35 | change "styler" to --stylet-- |
| 6 | 37 | change "styler" to --stylet-- |
| 7 | 42 | change "styler" to --stylet-- |
| 8 | 66 | change "styler" to --stylet-- |

Signed and Sealed this

Twenty-first Day of October 1997

Attest:

BRUCE LEHMAN

Attesting Officer

Commissioner of Patents and Trademarks